(12) United States Patent
Pauler et al.

(10) Patent No.: US 11,523,889 B2
(45) Date of Patent: Dec. 13, 2022

(54) LIGHT CURING APPLIANCE, IN PARTICULAR DENTAL LIGHT CURING APPLIANCE

(71) Applicant: Ivoclar Vivadent AG, Schaan (LI)

(72) Inventors: Markus Pauler, Feldkirch (AT); Alexander Kögel, Feldkirch (AT)

(73) Assignee: Ivoclar Vivadent AG, Schaan (LI)

(*) Notice: Subject to any disclaimer, the term of this patent is extended or adjusted under 35 U.S.C. 154(b) by 390 days.

(21) Appl. No.: 15/037,819

(22) PCT Filed: May 8, 2015

(86) PCT No.: PCT/EP2015/060180
§ 371 (c)(1),
(2) Date: May 19, 2016

(87) PCT Pub. No.: WO2015/173136
PCT Pub. Date: Nov. 19, 2015

(65) Prior Publication Data
US 2016/0287364 A1    Oct. 6, 2016

(30) Foreign Application Priority Data
May 12, 2014 (EP) ..................................... 14167896

(51) Int. Cl.
*A61C 13/15*   (2006.01)
*A61B 1/24*    (2006.01)
(Continued)

(52) U.S. Cl.
CPC .............. *A61C 19/004* (2013.01); *A61B 1/24* (2013.01); *A61B 5/0088* (2013.01); *A61B 5/062* (2013.01);
(Continued)

(58) Field of Classification Search
CPC ..... A61C 19/066; A61C 19/003; A61C 19/06; A61C 19/063; A61C 19/004;
(Continued)

(56) References Cited

U.S. PATENT DOCUMENTS 5,738,678 A * 4/1998 Patel .................... A61C 1/0046
433/215
6,103,203 A * 8/2000 Fischer ............... A61C 19/004
422/129
(Continued)

FOREIGN PATENT DOCUMENTS

AT    2863798 A1 * 8/2013 .......... A61B 5/1076
DE    3225589 A1    1/1984
(Continued)

*Primary Examiner* — Heidi M Eide
(74) *Attorney, Agent, or Firm* — Ann M. Knab; Thad McMurray

(57) ABSTRACT

The invention relates to a light curing appliance, in particular a dental light curing appliance (10), with a light source and with a light emission element such as an optical waveguide (12), of which the light output end is intended in particular to be directed towards a material that is to be polymerized. It is provided with one or more control devices (16) for switching on the light source during a polymerization cycle, and with one or more sensors (20) or sensor combinations connected to the control devices (16). The sensor (20) is designed as a location sensor and/or as a motion sensor (20) which detects a movement of the light curing appliance (10), designed as a hand-held appliance, and sends signals reproducing the motion to the control devices (16).

20 Claims, 9 Drawing Sheets

(51) Int. Cl.
   *A61B 5/00* (2006.01)
   *A61B 5/06* (2006.01)
   *A61C 1/00* (2006.01)
   *A61B 34/20* (2016.01)

(52) U.S. Cl.
   CPC ............ *A61B 5/742* (2013.01); *A61C 1/0015* (2013.01); *A61B 2034/2048* (2016.02)

(58) Field of Classification Search
   CPC ....... A61C 1/0007; A61C 1/0015; A61B 1/24; A61B 5/0088; A61B 5/062; A61B 5/742; A61B 2034/2048; A61N 5/06–0625; A61N 2005/0606; A61N 2005/0626–0629; A61N 2005/0642–0644
   USPC ............. 433/27, 29; 606/2, 13, 14; 600/245, 600/246; 362/572–575
   See application file for complete search history.

(56) References Cited

U.S. PATENT DOCUMENTS

| | | | | |
|---|---|---|---|---|
| 6,423,055 | B1* | 7/2002 | Farr | A61B 18/245 128/898 |
| 6,572,609 | B1* | 6/2003 | Farr | A61B 18/245 128/898 |
| 8,921,440 | B2* | 12/2014 | Weinmann | A61K 6/90 522/31 |
| 9,161,828 | B2 | 10/2015 | Senn et al. | |
| 9,622,833 | B2* | 4/2017 | Monty | A61C 1/0046 |
| 9,693,845 | B2* | 7/2017 | Price | G06Q 30/02 |
| 10,159,548 | B2* | 12/2018 | Peterson | A61C 19/004 |
| 2005/0003323 | A1 | 1/2005 | Katsuda et al. | |
| 2006/0122619 | A1* | 6/2006 | Kablik | A61B 17/00491 606/88 |
| 2006/0188835 | A1* | 8/2006 | Nagel | A61C 19/004 433/29 |
| 2006/0240376 | A1* | 10/2006 | Plank | A61C 19/004 433/29 |
| 2006/0252005 | A1* | 11/2006 | Feinbloom | A61C 19/004 433/29 |
| 2007/0259309 | A1* | 11/2007 | West | A61C 19/004 433/29 |
| 2008/0026339 | A1* | 1/2008 | Plank | A61C 19/004 433/29 |
| 2009/0323733 | A1* | 12/2009 | Charkas | A61C 1/0046 372/5 |
| 2010/0003633 | A1* | 1/2010 | Senn | G01N 21/55 433/29 |
| 2010/0140450 | A1* | 6/2010 | Duret | A61C 19/004 250/205 |
| 2010/0273123 | A1* | 10/2010 | Mecher | A61C 19/004 433/29 |
| 2011/0177474 | A1* | 7/2011 | Jamnia | A61B 17/320068 433/119 |
| 2012/0203213 | A1* | 8/2012 | Kimball | A61B 17/320068 606/1 |
| 2012/0257390 | A1* | 10/2012 | Fowler | A61C 19/004 362/249.02 |
| 2013/0059264 | A1* | 3/2013 | Monty | A61C 1/0046 433/29 |
| 2013/0244196 | A1* | 9/2013 | Goodacre | A61C 3/02 433/27 |
| 2013/0268033 | A1* | 10/2013 | Maass | A61N 5/0618 607/88 |
| 2013/0323673 | A1* | 12/2013 | Hakomori | A61B 5/682 433/29 |
| 2014/0186794 | A1* | 7/2014 | Deichmann | A61B 5/0088 433/75 |
| 2014/0303452 | A1* | 10/2014 | Ghaffari | A61B 1/05 600/301 |
| 2014/0363784 | A1* | 12/2014 | Monty | A61C 1/0046 433/29 |
| 2015/0250572 | A1* | 9/2015 | Gramann | A61B 1/247 433/29 |
| 2015/0374454 | A1* | 12/2015 | Beerstecher | A61C 19/004 433/27 |
| 2016/0008115 | A1* | 1/2016 | Senn | A61C 1/0015 433/27 |
| 2016/0074144 | A1* | 3/2016 | Peterson | A61C 19/004 433/29 |
| 2018/0263483 | A1* | 9/2018 | Elazar | A61B 1/00027 |
| 2018/0360317 | A1* | 12/2018 | Fisker | A61B 5/0088 |
| 2019/0239962 | A1* | 8/2019 | Deichmann | A61C 1/082 |

FOREIGN PATENT DOCUMENTS

| | | |
|---|---|---|
| DE | 8219588 U1 | 2/1985 |
| DE | 9204621 U1 | 7/1992 |
| EP | 1236444 A1 | 9/2002 |
| WO | 9426203 A1 | 11/1994 |
| WO | 2014043488 A1 | 3/2014 |
| WO | 2014135589 A1 | 12/2014 |

* cited by examiner

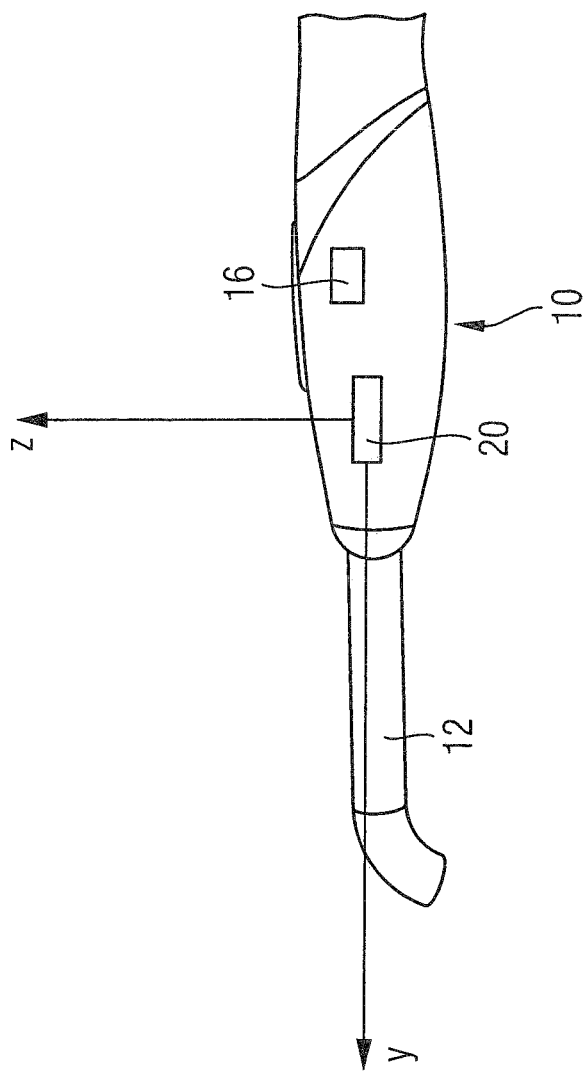
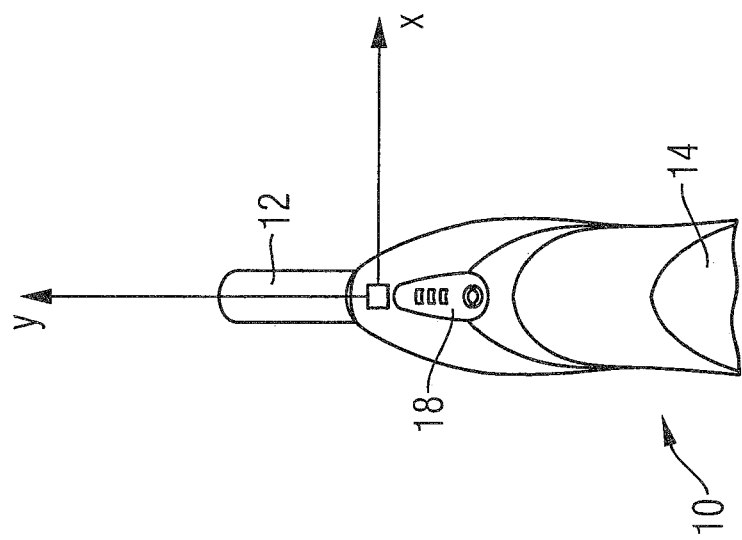

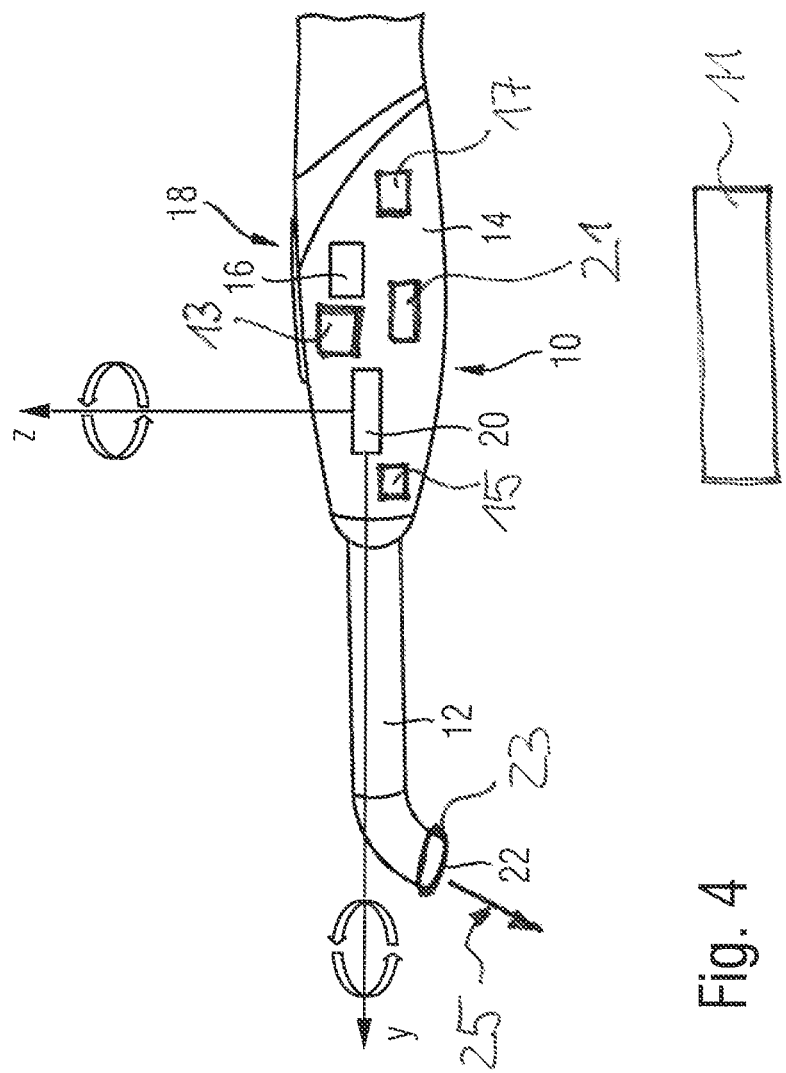
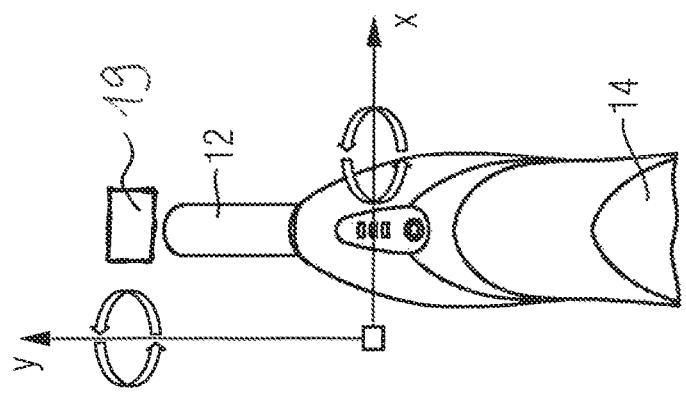
Fig. 4
Fig. 3

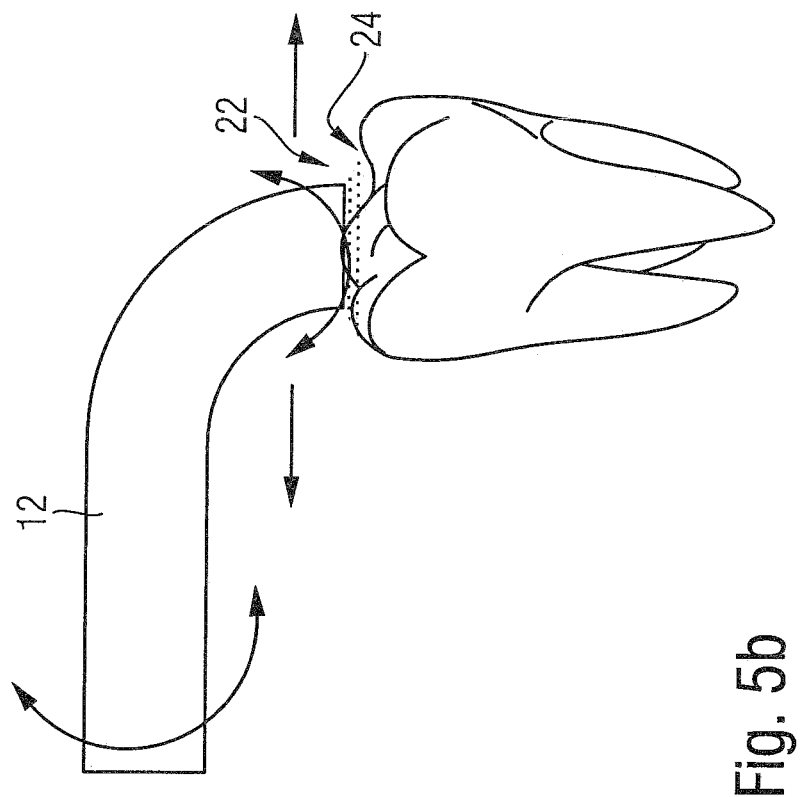
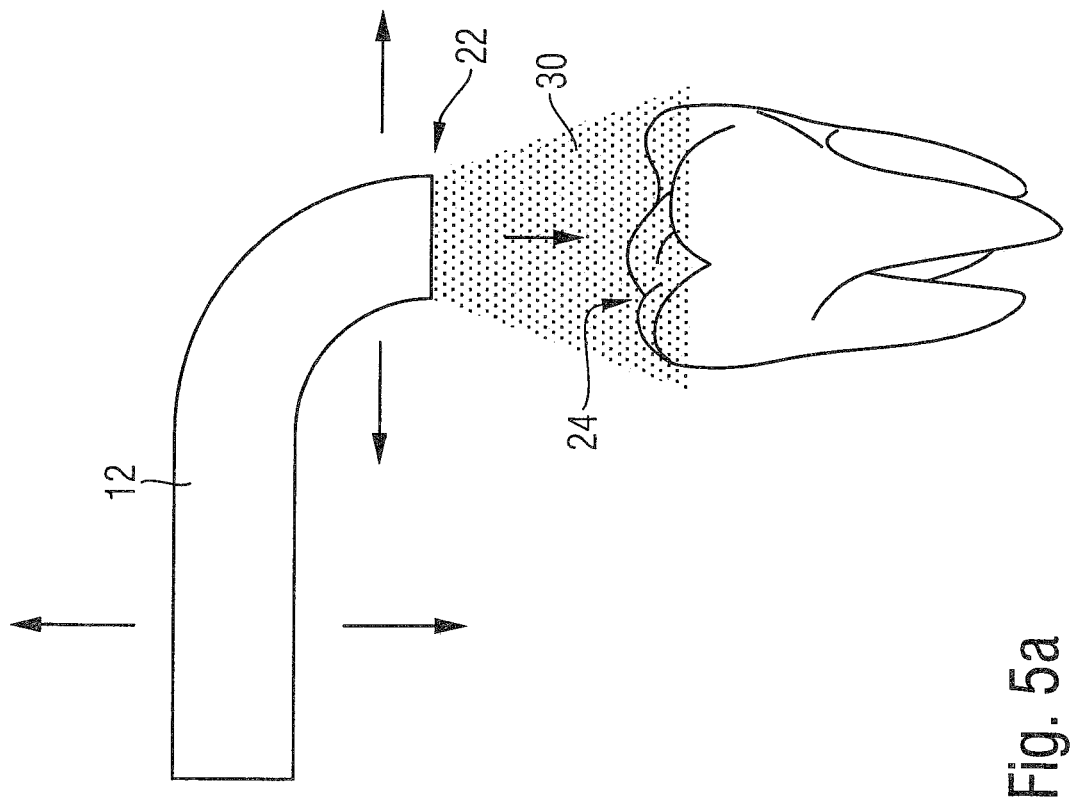

LIGHT CURING APPLIANCE, IN PARTICULAR DENTAL LIGHT CURING APPLIANCE

CROSS-REFERENCE TO RELATED APPLICATIONS

This application is a National Stage application of International patent application PCT/EP2015/060180 filed on May 8, 2015, which claims priority to European patent application No. 14167896.1 filed on May 12, 2014, the disclosures of which are incorporated herein by reference in their entirety.

FIELD OF THE INVENTION

The invention relates to a light curing appliance, in particular a dental light curing appliance for material to be polymerized such as PMMA or composites and adhesives and cements as well as for the excitation of any desired photoinitiators.

BACKGROUND

Light curing appliances of this type have been known for long and are used on a large scale when composites or PMMA dental restorations are to be polymerized and cured.

For the polymerization of dental restorations it is necessary to supply them with a predetermined amount of light which means that supplying the dental restoration with the amount of light is decisive and not the emission of the amount of light by means of the light curing appliance.

It has been known for long to use so-called light-dosage sensors for this purpose, and it is referred to DE 92 04 621 U1 by way of example. By means of the dosage device thereat the reflected light is to be detected, and depending on this the amount of light is to be provided which is necessary to enable a complete polymerization of the dental restoration material.

If the light output end of the light curing appliance, which is designed as a hand-held appliance, is directed towards the space of the mouth cavity—but not towards the teeth—barely any light is reflected such that the dosage unit thereat takes into account this incorrect light in the assessment of the amount of light to be emitted.

If, on the other hand, the light output end is directed towards a tooth, but next to the restoration material, the emitted light is reflected towards the dosage unit. This reflected light is not taken into account as incorrect light by the dosage unit, and the time in which light is emitted by the light source of the light curing appliance is taken into account when the polymerization cycle, that is to say the entire exposure time of the dental restoration part, is calculated.

This leads to a miscalculation as by exposing neighboring teeth—or for instance neighboring dental restorations which have already been cured—no or an insufficient polymerization takes place as a matter of fact.

Admittedly, by means of a polarizing filter, which is said to be expendable, a differentiation between the types of reflected light is to be realized. However, this is not possible at least if the light is reflected from a neighboring dental restoration which has already been cured.

For this reason, this solution has not become accepted which is not really a surprise in this respect.

With stationary light curing appliances sensors have become known which serve to control the light curing appliance. By way of example, it is referred to DE 32 25 589 A1 and DE 82 19 588 U1. By means of optical sensors a stationary light curing appliance is turned on in these solutions when the dental restoration part to be treated approaches the light curing appliance.

However, with these solutions, too, an incorrect exposure is possible, for instance if the finger of the user approaches the optical proximity sensor before the dental restoration part has been put into the light cone.

The light curing appliances known so far produce incorrectly cured parts regularly in case of maloperations, which is all the more critical as nowadays monomers with their free radicals which stay in the mouth of the patient are often considered a case of liability for the dentist.

SUMMARY

Contrary to this, the invention is based on the task of providing a light curing appliance according to the preamble of claim 1 which offers an improved secure operation as well as improved ergonomics.

This task is inventively solved by independent claims. Advantageous developments may be taken from the subclaims.

By implementing a location sensor and/or a motion sensor and/or an angular sensor and/or a magnetic field sensor and/or a combination thereof as part of a light curing appliance several advantages can be achieved at the same time. The employed sensor can, for instance, be used to ensure that the light curing appliance stays in the position at which the dentist has placed it when polymerization has been turned on.

This is to ensure that the polymerization process is completed if a polymerization process takes place at all. Contrary to this, the dentist easily recognizes the unpolymerized dental restoration part as it is soft or almost liquid. In this connection, it is referred to the fact that the dentist cannot recognize without further ado if the surface of the increment has cured but not the material within/on the bottom of the filling.

According to an advantageous aspect of the invention, the invention is based on the idea that, when the dentist positions the light curing appliance at the correct position and activates the exposure, that is to say starts the polymerization cycle, the latter is performed properly unless the appliance is moved away from the correct position accidentally.

This can be ensured by means of the inventive location sensors or motion sensors or magnetic field sensors or gyrometers or a combination thereof which detect when the light curing appliance is moved away from the correct position after the exposure has been started.

For this purpose, the inventive sensors are preferably configured as relative sensors and/or absolute sensors. A location sensor of this type recognizes a movement of the hand-held appliance, as which the light curing appliance is configured, in one of the three spatial directions or dimensions, and preferably an angular change.

In this connection, it is preferred according to the invention to provide limiting values from which a movement is considered to be critical. For example, an angular deviation of the orientation of the light beam which is emitted from the light output end can be much more critical than a shift of the light curing appliance in an axial direction, that is to say in the direction of the light emission element, by one or several millimeters. The angular deviation would lead to the target area of the light emission element, that is to say the dental restoration or the treatment area, being missed considerably while shifting the hand-held appliance in an angle-preserving manner in a rearward direction only leads to a reduction of the applied light efficiency which is usually a small reduction.

In an advantageous embodiment of the invention it is possible to evaluate the parameters detected by the invention location sensor and/or motion sensor which are supplied to the inventive control device as signals in order to trigger an action or function of the light curing appliance.

For instance, picking up a hand-held appliance, as which the light curing appliance is configured, from a base can be detected for this purpose and the detection can be used to switch the light curing appliance into an active state in which the polymerization cycle can be started immediately, if desired.

In this embodiment the light curing appliance is preferably in a state of rest in the laid-down condition which state of rest saves the accumulators used for operating the appliance. Picking up the light curing appliance is connected to a movement which is detected by the inventive sensors.

It is also possible to trigger a certain function such as a change of program by means of targeted movements, such as shaking, as has become known with smart phones.

It is to be understood that the current state of the inventive light curing appliance is preferably signalized by a display, such as a liquid-crystal display, suitable for this purpose.

In case of an accidental shifting, such as an excessive angular deviation during the polymerization process, or, for instance, if the hand-held appliance is dropped, an alarm can be triggered and/or the concerned event can be recorded which can also be used as a proof for warranty claims.

The detection of the location can be implemented in a way known per se by triangulation with respect to at least three predetermined sources of reference. Among the possible media are electromagnetic, but also ultrasound or infrared sources. It is also possible to carry out image recognition via a camera and hereby to detect the change of position. Preferably, the shift or movement is detected relatively, that is to say preferably in terms of a point of reference, a position of reference or an angular position of reference.

It is also possible to optionally temporarily increase the light power and/or prolong the exposure time in case of a small deviation from the desired position and/or angular orientation, to still ensure a proper polymerization process and to reach the necessary overall dosage of light. By detecting the positional deviation above a first threshold value at least one compensation step is initiated in this solution, while in case of a detection of a deviation above a second or further threshold value (more than two are possible) signalization takes place, storing and/or turning off the light curing appliance.

The possibilities to compensate for the incorrect positioning also include the tracking of the light cone or the change of focus which requires a shift of corresponding lenses and/or reflectors.

It is also possible to direct a mini camera towards the treatment area and to ensure that the tracking via image recognition takes place automatically in case a shift is detected. In this case, the mini camera serves as a motion sensor or location sensor in this respect.

BRIEF DESCRIPTION OF THE DRAWINGS

Further advantages, details and features may be taken from the following description of several exemplary embodiments in conjunction with the drawings, in which:

FIG. 1 shows a schematic view of an inventive light curing appliance including two space coordinates;

FIG. 2 shows the exemplary embodiment according to FIG. 1 in a crosswise view which accordingly represents two other space coordinates;

FIG. 3 shows a modified embodiment of the inventive light curing appliance comprising a rotation sensor;

FIG. 4 shows an illustration of the light curing appliance according to FIG. 3 in another view;

FIGS. 5a and 5b show two illustrations of handling a part of the inventive light curing appliance, wherein the distance and the relative position to a tooth which is to be treated are detected;

DETAILED DESCRIPTION

Figure 6:
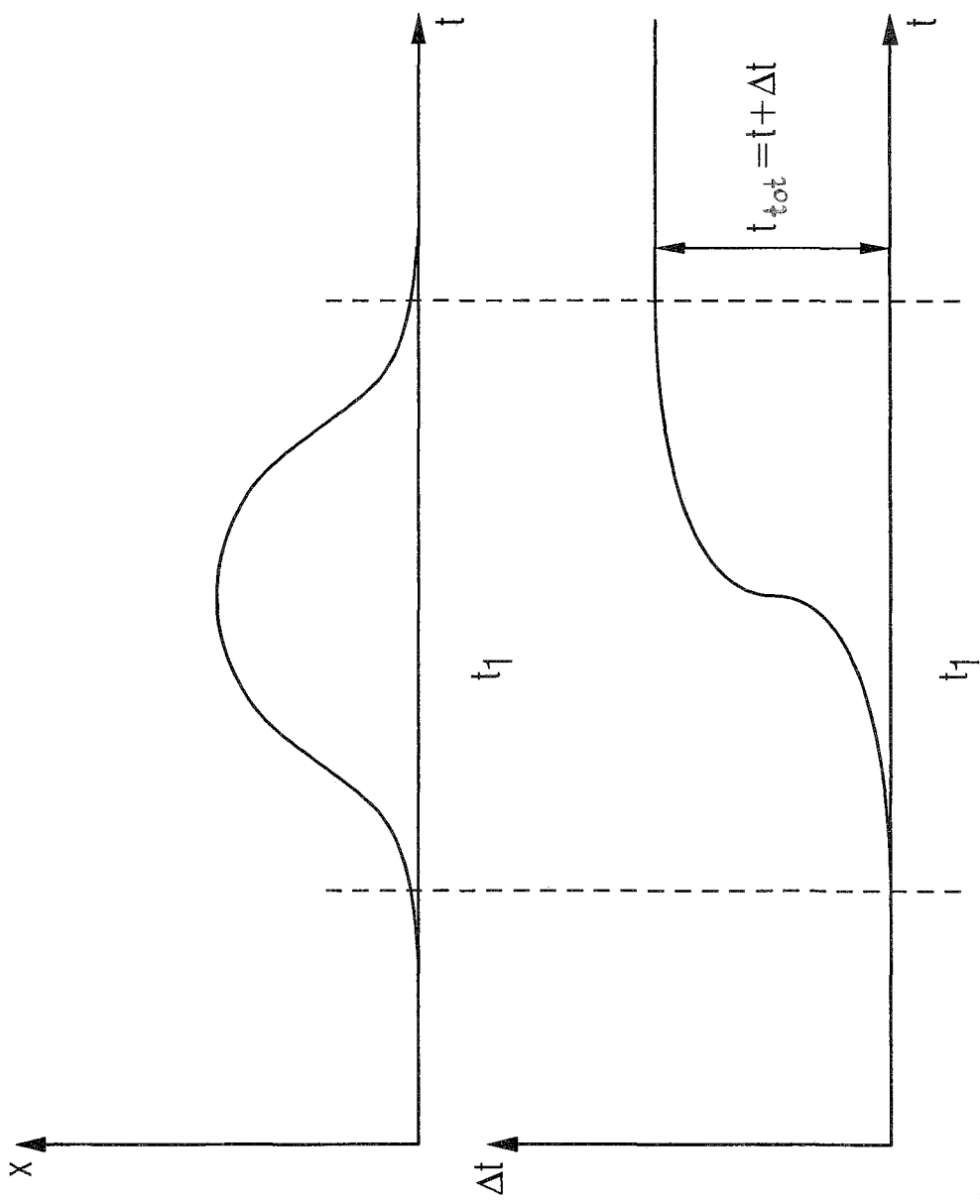
FIG. 6 shows an illustration of the prolongation of the exposure time when an angular deviation is detected.

The light curing appliance 10 illustrated in FIG. 1 comprises a cranked optical waveguide 12 and a housing 14 in a way known per se. The housing 14 receives a light source which supplies the optical waveguide 12 with the emitted light, and also an energy source, in the exemplary embodiment illustrated in the form of an accumulator. A control device 16 schematically illustrated in FIG. 2 controls the polymerization cycle of the light curing appliance 10. Additionally, a switch 18 is provided at the housing 14, in the exemplary embodiment at the upper side of the light curing appliance 10 which is substantially pin-shaped and/or pistol-shaped.

According to the invention, the light curing appliance 10 further comprises a sensor 20 which is configured as a translational motion sensor in the exemplary embodiment illustrated. Thus, the sensor 20 forwards motion data of the light curing appliance 10 which it detects to the control device 16; the latter triggers the necessary action of the light curing appliance 10 based on the movement.

In this exemplary embodiment, the motion sensor 20 is configured as a translational motion sensor. It detects movements of the light curing appliance in three spatial directions of which the spatial directions x and y are illustrated in FIG. 1 and of which the spatial directions y and z are illustrated in FIG. 2.

As an exemplary use it is provided with this embodiment that the light curing appliance 10 detects a movement of any type when it is turned off or in a position of rest. When the dentist picks up the light curing appliance a movement occurs, and based on the respectively detected motion signal of the sensor 20 the control device 16 transfers the light curing appliance 10 from a state of rest into a state of stand-by.

While in the state of rest all the energy-intensive circuits of the light curing appliance are turned off and only the motion sensor is supplied with a very low current, in the state of stand-by the light curing appliance 10 is ready to start a polymerization cycle immediately, that is to say without any delay. The circuits required for this purpose, that is to say the actual control of the light curing appliance, are supplied with electricity for this purpose. In practice, the electricity requirement of the light curing appliance is very low in the state of rest and amounts to for instance 1 µA or even only 100 nA, while in the state of stand-by a consumption of electricity of for instance 20 mA is produced.

It is also possible to load a capacitor of high capacitance such as 10F in the state of stand-by, and to supply this capacitor, for instance, with a current of 1 A for this purpose when the state of stand-by is started.

Accordingly, the consumption of electricity during the state of stand-by can be in the order of magnitude of the consumption of electricity of the polymerization cycle in this embodiment.

According to the invention it is particularly favorable with this embodiment that a state of rest is possible in which the consumption of electricity is reduced drastically, that is to say by several powers of ten, and that thus the operating time of the accumulator used is increased accordingly without delays with respect to the starting program of the micro processor for the polymerization cycle arising as a consequence—of course, the micro processor is turned off in the state of rest.

FIG. 3 shows a light curing appliance which is modified compared with this. This and all further light curing appliances are provided with corresponding or the same reference signs for corresponding parts such that the reference signs do not have to be explained again.

With the micro processor according to the FIGS. 3 and 4 the sensor 20 is also configured as a motion sensor, but as a rotation sensor. In comparison, this sensor has a different function which is connected to the polymerization.

In the polymerization process it has to be taken into account that the tip 22 of the optical waveguide 12 is in immediate and, if possible, almost direct contact with the dental restoration to be polymerized. Typically, the dentist picks up the light curing appliance 10 at the housing 14 from a base station 11. The switch 18 is provided with suitable displays such as LED displays to signalize the operating condition such that this area is often left blank when the light curing appliance is picked up.

FIG. 4 shows a light sensor 13 and a camera 15, which are connected to the light curing appliance (10) via control device 16, and the light sensor 13 and/or camera 15 are directed towards the material to be polymerized or a treatment area, and based on the output signals of the light sensor 13 and/or the camera 15 the ideal position of the light curing appliance (10) for the polymerization cycle can be determined.

If, during the polymerization process, the dentist is distracted, for instance, or accidentally performs an involuntary movement of the hand, the tip 22 is moved away from the target area, that is to say the dental restoration. Due to the length of the light curing appliance 10 a very small rotation about the axis Z according to FIG. 4 already leads to a strong displacement of the tip 22.

According to the invention, the inventive sensor 20 which is configured as a rotation sensor counteracts an incorrect polymerization induced as a result of this as the control device 16 creates a suitable signalization based on the output signal of the sensor 20 during the polymerization cycle.

It is also possible to indicate the direction of movement of correction; if, for instance, the tip 22 is pivoted to the left accidentally, in the area of the display of the switch 18 a signal is shown which reads "turn to the right".

This can be realized by means of respective pictograms, any other visualization or, for instance, by means of voice output.

Control device 16 is able to adjust and control the exposure time, that is to say the length of the polymerization cycle, depending on the signal of the sensor(s) (20) and prolongs the exposure time in case of an incorrect position and/or a movement of the handpiece or turns off the light curing appliance upon reaching a cancellation criterion/threshold value. Control device (16) can increase the exposure rate, in particularly temporarily, in case of an incorrect position/motion as from one or more predetermined threshold values, or turns off the light curing appliance upon reaching a cancellation criterion/threshold value.

Control device (16) can signal an incorrect position of the light curing appliance (10) during the polymerization cycle, in particular based on the detected signals of the sensor(s) (20) by means of a suitable reply to the user, in particular by vibration and/or an acoustic/visual signalizing (illuminated LED/housing (14)) and/or by turning off the light curing appliance (10).

Control device (16) can activate and/or deactivate a predetermined program function responsive to an acceleration with a predetermined course of time, such as tapping.

FIG. 4 also includes an additional control device 17, a deflector 19, and an additional sensor 21. A reference light beam 25 is shown exiting tip 22 creating a reference field for detection of a change of location and/or the motion and/or the acceleration in the reference field in at least two dimensions. Examples of deflector 19 may include but are not limited to a lens 23 shown in FIG. 4 or a reflector 40 shown in FIG. 11. The motion sensor may be configured as an acceleration sensor. In the case that the acceleration exceeds a predetermined value the control device (16) evaluates and stores this acceleration in order to prove excessive shocks (damage due to impacts, drop, etc.) of the light curing appliance (10).

A reference field may be created with the base station for the light curing appliance, which base station creates a reference field when removing the light curing appliance from the base station, and wherein a combined gyrometer angular sensor can detect a change of the location and/or the motion and/or acceleration in the reference field, in at least two dimensions.

Figure 11:
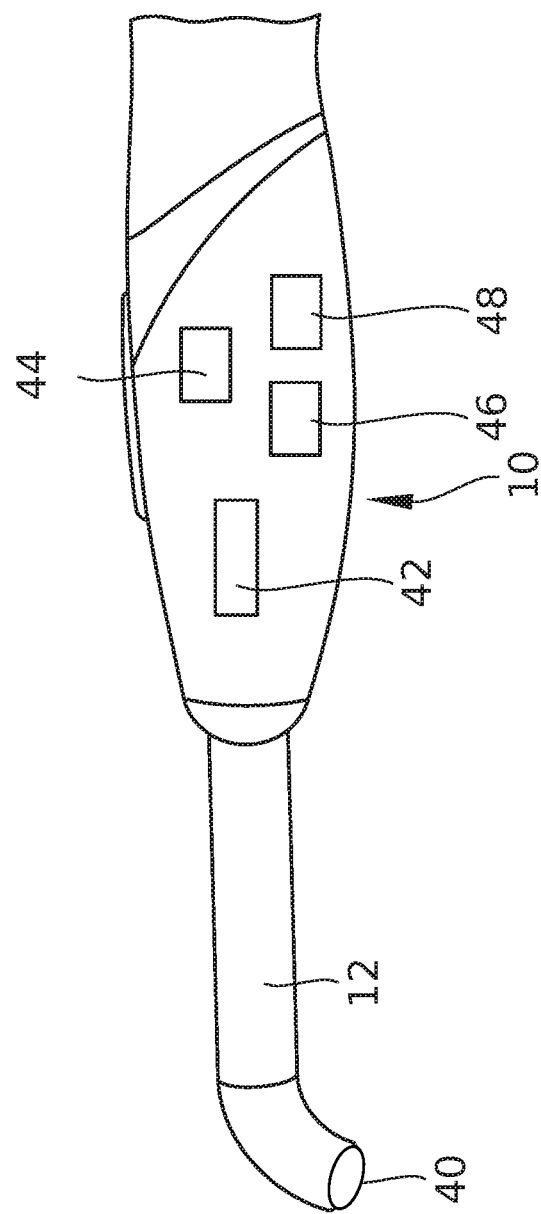
FIG. 11 shows a further embodiment of an inventive light curing appliance.

A combination of an acceleration sensor 46, gyrometer 48 and magnetic field sensor 44 as shown in FIG. 11 and their individual signals can be processed to form an overall signal, and any noise or incorrect information can be compensated for to produce a constant signal. The gyrometer sensor 48 can be a gyrometer angular sensor configured from the combination of a location sensor and motion sensor.

Motion sensor (20), can be an acceleration sensor or gyrometer, configured as a relative motion sensor which detects relative motion in terms of the position and/or inclination of the hand-held appliance at the beginning of exposure, that is to say at the beginning of the polymerization cycle, in particular in at least two dimensions, preferably in all three dimensions.

FIGS. 5a and 5b illustrate the polymerization situation during the polymerization cycle. In the illustration according to FIG. 5b, the tip 22 of the optical waveguide 12 is directly adjacent to the dental restoration 24 and polymerization takes place at a maximum intensity of exposure, that is to say correspondingly fast.

Contrary to this, in the illustration according to FIG. 5a, the tip 22 of the optical waveguide 12 is spaced apart from the dental restoration 24 at a considerably larger distance. Due to the widening of the beam 30 the intensity of exposure of the dental restoration 24 is lower, and it is possible to either output a position correction signal or to automatically prolong the exposure time. One means of detecting distance is by the changing brightness of the beam.

It is to be understood that it is possible to combine both possibilities, that is to say to prolong the exposure time until the dentist becomes aware of the incorrect positioning and returns the tip 22 to the position according to FIG. 5b.

It is to be understood that incorrect curings can also result from laterally displacing the tip 22. Depending on the dimensions of the dental restoration 24 relative to the emission diameter of the tip 22 these incorrect curings are even more critical than a change of distance which is to be compensated for by the position sensor 20 according to the invention.

Examples of position sensor or location sensor 42 include, but are not limited to, GPS satellite triangulation, radio transmitters, electromagnetic fields and/or ultrasound and/or infrared sources. The location sensor 42 can be configured and combined with the motion sensor 20 as a combined gyrometer angular sensor 48.

FIG. 6 illustrates how the prolongation of the exposure time is ensured by way of calculation. The upper curve from FIG. 6 shows an accidental displacement, for instance in the x direction. If the displacement exceeds a certain threshold value, for instance at the point in time $t_1$, an error signal is transmitted to the dentist. After his/her reaction time, the light curing appliance should be returned to the correct position.

Without the inventive sensor the effective polymerization time would be too short, and thus, according to the invention, the polymerization time is prolonged by the value ΔT, in accordance with the time in which the displacement in the incorrect position takes place.

As a result, the polymerization time is prolonged to $t_{tot}$ according to the invention. However, this is not as significant as an incorrect polymerization which is known to have serious consequences.

Figure 7:
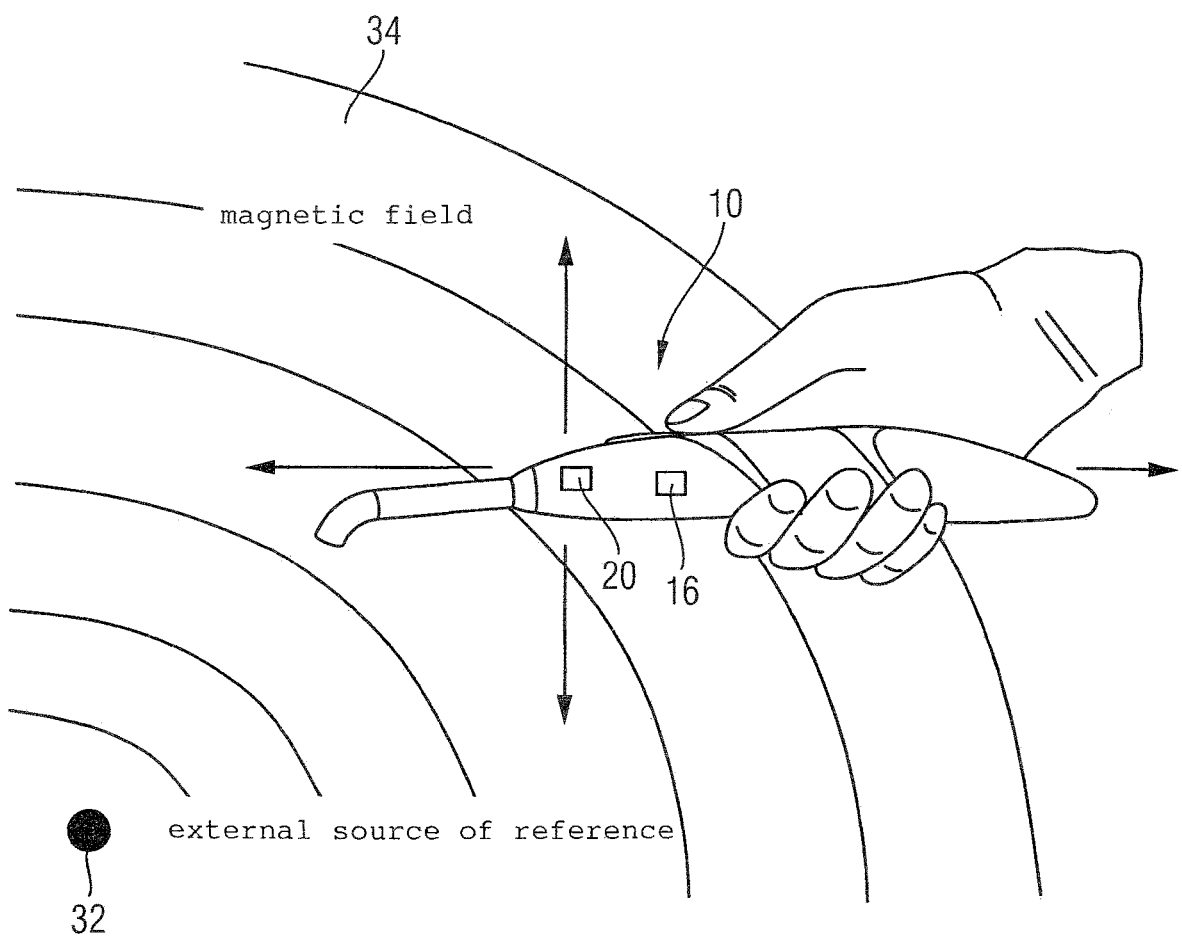
FIG. 7 shows an illustration of a further embodiment of an inventive light curing appliance in which a magnetic field is detected.

FIG. 7 illustrates a further possibility of detecting a position of the inventive light curing appliance.

It is to be understood that the light curing device is configured as a hand-held appliance in any case and comprises either an external or an internal source of electricity. In this embodiment which is illustrated schematically in FIG. 7 an external source of reference 32 is implemented which produces a magnetic field. In this solution, the distance and the distances to the external source of reference can be determined and thus at least a determination of position can be performed.

In practice, at least 1, preferably 3 external sources of reference 32 are implemented in this embodiment and produce respective magnetic fields 34, and in a way known per se the exact position can be determined by triangulation.

The sensor 20 is configured as a magnetic field sensor in the exemplary embodiment illustrated.

Figure 8:
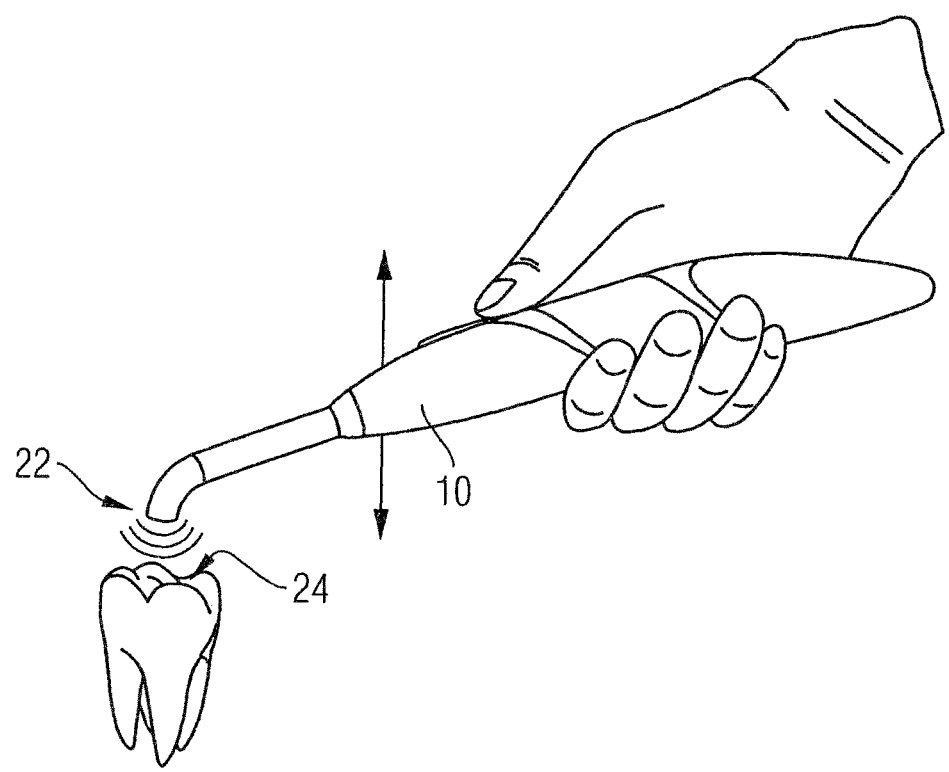
FIG. 8 shows a further embodiment of an inventive light curing appliance comprising an ultrasound or laser distance measuring device.

In the embodiment according to FIG. 8 it is provided to configure a distance sensor at the tip 22 of the light curing appliance 10. The distance sensor can, for instance, be realized by means of ultrasound or as a laser distance measuring device. In this way, the relative position of the light curing appliance 10 with respect to the treatment area, that is to say the dental restoration, can be determined directly.

Figure 9C:
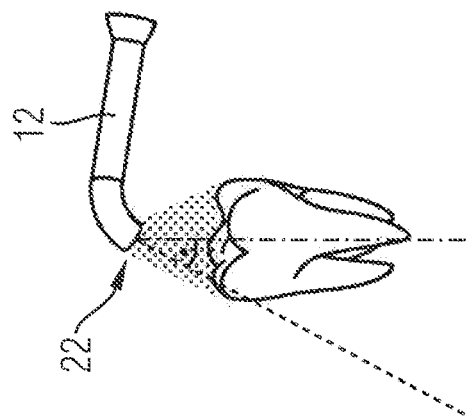
FIG. 9c shows a further embodiment of an inventive light curing appliance.
Figure 9B:
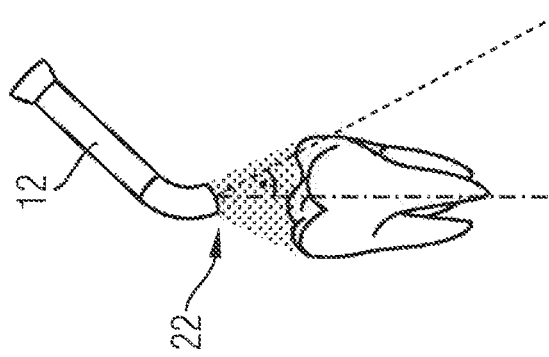
FIG. 9b shows a further embodiment of an inventive light curing appliance.
Figure 9A:
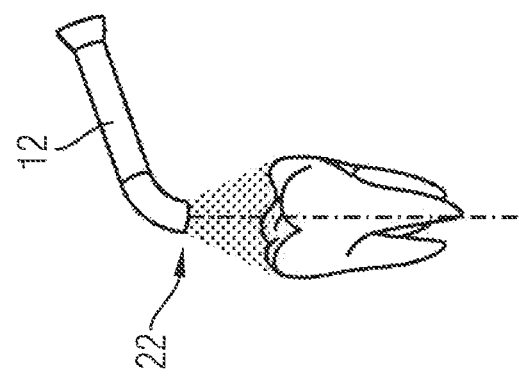
FIG. 9a shows a further embodiment of an inventive light curing appliance.

FIG. 9 illustrates that by means of a rotation sensor the angular orientation of the emission axis can be detected and corrected, if necessary.

Figure 10:
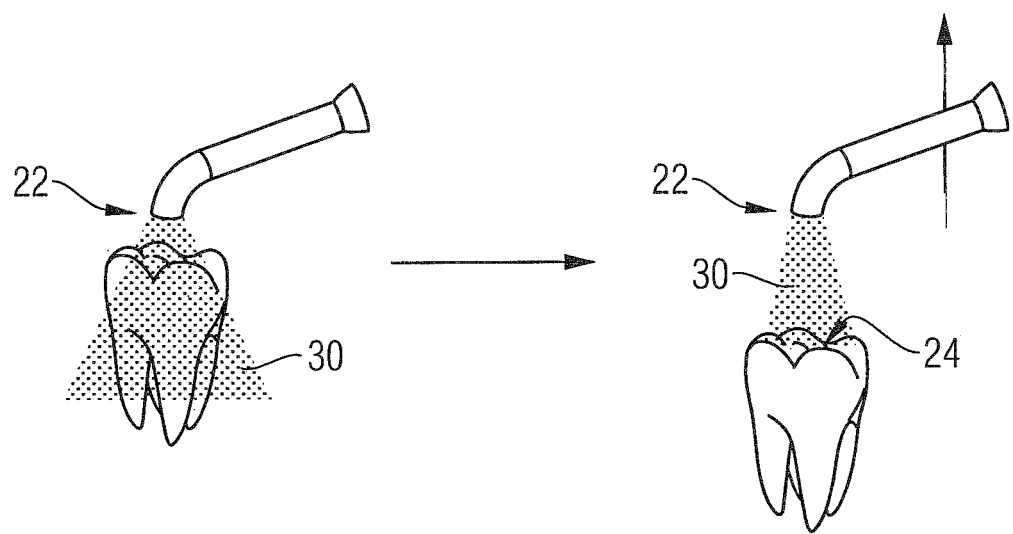
FIG. 10 shows a further embodiment of an inventive light curing appliance.

FIG. 10 shows schematically how the light widening 30 in combination with the distance of the tip 22 to the dental restoration 24 influences the exposure. With the relatively large beam widening 30 illustrated on the left-hand side, a small distance is enough to expose even a large-area dental restoration. Contrary to this, with the beam widening 30 illustrated on the right-hand side, a larger distance is necessary to expose the entire large-area dental restoration.

In this respect, there is always an ideal distance between the tip 22 and the dental restoration 24, and the inventive motion sensor can not only determine this distance.

Rather, in the embodiment according to FIG. 10 it is provided to also adjust the focus of the beam widening 30 to the distance, which can be realized in a way known per se by means of optical means.

The invention claimed is:

1. A dental light curing appliance (10) comprising:
   a light source,
   a light emission element, wherein the light source supplies light to the light emission element,
   a light output end intended to be directed towards a material that is to be polymerized,
   one or more control devices (16) configured for switching on the light source during a polymerization cycle, and
   at least two sensors connected to the one or more control devices and passing on measured values detected by the at least two sensor(s) to the one or more control devices wherein
   the light source, light emission element, light output end, the one or more control devices and the at least two sensors configured together as a hand-held appliance,
   the at least two sensors comprise
   a location sensor and a motion sensor wherein the motion sensor detects movement of the dental light curing appliance and sends signals reproducing the motion to the one or more control devices and
   wherein the motion sensor, is configured as a relative motion sensor which detects the movement in terms of a position and/or inclination of the hand-held appliance at a beginning of the polymerization cycle, which the beginning of the polymerization cycle comprises a correct position, in at least two dimensions, and
   wherein the one or more control devices is/are configured to evaluate the signals from the motion sensor and/or location sensor and is/are configured to prolong the polymerization cycle when a deviation of the hand-held appliance from the correct position occurs by accidental movement of the hand-held appliance during the polymerization cycle based on the signals of the location sensor and/or the motion sensor, said prolongation of the polymerization cycle is proportional to the degree of deviation and duration of the deviation.

2. The dental light curing appliance as claimed in claim 1, wherein the location sensor detects the position of the light emission element relative to the material to be polymerized.

3. The dental light curing appliance as claimed in claim 1, wherein the location sensor comprises a light sensor and/or a camera, said light sensor and/or camera are directed towards the material to be polymerized, and wherein based on output signals of the light sensor and/or the camera the correct position of the light curing appliance for the polymerization cycle can be determined.

4. The dental light curing appliance as claimed in claim 3, wherein the at least two sensors further comprise a gyrometer angular sensor which detects an angular change of a light beam emitted by the light output end, wherein the combination of the location sensor, the motion sensor and the gyrometer angular sensor are configured and combined to detect the deviation.

5. The dental light curing appliance as claimed in claim 4, wherein the light curing appliance also comprises a base station which creates a reference field when removing the light curing appliance from the base station, and wherein the combined location sensor, motion sensor and gyrometer angular sensor detects a change of the location and/or the motion and/or acceleration in the reference field, in at least two dimensions.

6. The dental light curing appliance as claimed in claim 1, wherein the location sensor of the hand-held appliance is a position sensor and detects the position by GPS satellite triangulation, radio transmitters, electromagnetic fields and/or ultrasound and/or infrared sources.

7. The dental light curing appliance as claimed in claim 1, wherein the location sensor detects distance to the treatment area of the material to be polymerized, which detect the distance by a changing brightness of a predetermined reference light beam.

8. The dental light curing appliance as claimed in claim 7, wherein the one or more control devices turns off the light curing appliance upon reaching a threshold value.

9. The dental light curing appliance as claimed in claim 1, wherein the one or more control devices signalize(s) the deviation of the light curing appliance during the polymerization cycle, based on detected signals of the at least two sensor(s) by a vibration of the light curing appliance and/or an acoustic and/or visual signal, and/or by turning off the light curing appliance.

10. The dental light curing appliance as claimed in claim 9, wherein if the deviation is detected by the at least two sensor(s), a light cone emitted by the light output end is trackable by a deflector.

11. The dental light curing appliance as claimed in claim 9, wherein the detected signal comprises a visual signal in the form of an illuminated LED in the dental light curing appliance.

12. The dental light curing appliance as claimed in claim 1, wherein the one or more control device(s) is configured to activate and/or deactivate the polymerization cycle wherein the polymerization cycle comprises a predetermined program function having a predetermined course of time, said activation or deactivation based on an acceleration of the hand-held appliance.

13. The dental light curing appliance as claimed in claim 1, wherein the motion sensor is configured as an acceleration sensor and wherein if an acceleration is above a predetermined value the one or more control device(s) evaluate(s) and store(s) the acceleration.

14. The dental light curing appliance as claimed in claim 1 the polymerization cycle comprises moving the light curing appliance from a resting position which transfers the appliance into an activated condition.

15. The dental light curing appliance as claimed in claim 14, wherein focusing of light from the light output end is regulated or increased depending on the motion/position of the handpiece.

16. The dental light curing appliance as claimed in claim 1, wherein the motion sensor and the location sensor are configured as a combination of an acceleration sensor, gyrometer and magnetic field sensor to measure motion and location and wherein the signals from the motion and location sensors comprise individual signals from the acceleration sensor, gyrometer and magnetic field sensor which are processed to form an overall signal, and wherein noise or incorrect information are compensated for and a constant signal is produced.

17. The dental light curing appliance as claimed in claim 1, wherein the light emission element comprises an optical waveguide.

18. The dental light curing appliance as claimed in claim 1, wherein the location sensor comprises a magnetic field sensor.

19. The dental light curing appliance as claimed in claim 1, wherein the hand-held appliance further comprises a deflector, wherein the deflector comprises a reflector or a lens.

20. A dental light curing appliance comprising:
a light source,
a light emission element, wherein the light source supplies light to the light emission element,
a light output end intended to be directed towards a material that is to be polymerized,
one or more control devices configured for switching on the light source during a polymerization cycle, and
one or more sensors connected to the one or more control devices and passing on measured values detected by the one or more sensor(s) to the one or more control devices wherein
the light source, light emission element, light output end, the one or more control devices and the one or more sensors are configured together as a hand-held appliance,
the one or more sensors comprises
an acceleration sensor or gyrometer which detects movement of the dental light curing appliance and is configured as a relative motion sensor which detects movement in terms of a position and/or inclination of the hand-held appliance at a beginning of the polymerization cycle, which the beginning of the polymerization cycle comprises a correct position, in at least two dimensions, and
wherein the one or more control devices is/are configured to evaluate the measured values from the acceleration sensor and/or gyrometer and is/are configured to prolong(s) the polymerization cycle when a deviation of the hand-held appliance from the correct position occurs by accidental movement of the hand-held appliance during the polymerization cycle based on the measured values of the acceleration sensor or gyrometer, said prolongation of the polymerization cycle is proportional to the degree of deviation and duration of the deviation.

* * * * *